United States Patent
Hochman et al.

(10) Patent No.: US 8,425,231 B1
(45) Date of Patent: *Apr. 23, 2013

(54) SOFT-TISSUE PRESERVATION TEMPORARY (SHELL) IMMEDIATE-IMPLANT ABUTMENT METHOD AND DEVICE

(76) Inventors: Mark N. Hochman, Great Neck, NY (US); Stephen J. Chu, New York, NY (US); Jocelyn Huiping Tan-Chu, New York, NY (US); Adam J. Mieleszko, Arverne, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/356,359

(22) Filed: Jan. 23, 2012

(51) Int. Cl.
*A61C 8/00* (2006.01)

(52) U.S. Cl.
USPC .......................................... 433/173; 433/174

(58) Field of Classification Search .......... 433/172–176, 433/201.1, 215; 264/16–20
See application file for complete search history.

(56) References Cited

U.S. PATENT DOCUMENTS

| | | | |
|---|---|---|---|
| RE27,227 E | 11/1971 | Brodbeck | |
| 4,713,004 A | 12/1987 | Linkow et al. | |
| 4,955,811 A | 9/1990 | Lazzara et al. | |
| 5,213,502 A | 5/1993 | Daftary | |
| 5,297,963 A | 3/1994 | Dafatry | |
| 5,417,568 A | 5/1995 | Giglio | |
| 5,433,606 A | 7/1995 | Niznick et al. | |
| 5,527,182 A * | 6/1996 | Willoughby | 433/172 |
| 5,547,377 A | 8/1996 | Daftary | |
| 5,599,185 A | 2/1997 | Greenberg | |
| 5,685,714 A | 11/1997 | Beaty et al. | |
| 5,779,481 A | 7/1998 | Aires | |
| 5,810,589 A | 9/1998 | Michnick et al. | |
| 5,810,592 A * | 9/1998 | Daftary | 433/173 |
| 5,890,902 A * | 4/1999 | Sapian | 433/173 |
| 5,899,695 A | 5/1999 | Lazzara et al. | |
| 5,899,697 A | 5/1999 | Lazzara et al. | |
| 5,947,732 A | 9/1999 | Beaty et al. | |
| 5,989,026 A | 11/1999 | Rogers et al. | |
| 5,989,028 A | 11/1999 | Niznick | |
| 6,120,293 A | 9/2000 | Lazzara et al. | |
| 6,152,737 A | 11/2000 | Beaty et al. | |
| 6,168,435 B1 | 1/2001 | Beaty et al. | |

(Continued)

OTHER PUBLICATIONS http://www.osseonews.com/restoration-of-immediate-temporary-crown-cases-guidance/.

(Continued)

*Primary Examiner* — Yogesh Patel
(74) *Attorney, Agent, or Firm* — Notaro, Michalos & Zaccaria P.C.

(57) ABSTRACT

A dental implant arrangement and method has a hollow shell with outer bio-compatible surface for engaging a soft-tissue socket that is left in gingival tissue after a tooth has been extracted, to promote healing. The shell tapers outwardly from a first to a second perimeter, the second perimeter being asymmetrically scalloped with opposite distal and mesial peaks and opposite lingual and facial valleys between the peaks. A dental implant in the bone socket left after tooth extraction is rigidly connected to a temporary post, the temporary post extending in the shell. A luting compound fills the volume between shell and post and solidifies, thereby connecting shell to post and indirectly to the dental implant with no other connection between the shell and the implant so that the outer surface of the shell engages against the soft-tissue socket without gaps and without requiring alignment between the shell and implant axes.

15 Claims, 5 Drawing Sheets

U.S. PATENT DOCUMENTS

| | | | |
|---|---|---|---|
| 6,287,117 | B1 | 9/2001 | Niznick |
| 6,312,259 | B1 | 11/2001 | Kvarnstrom et al. |
| 6,343,930 | B1 | 2/2002 | Beaty et al. |
| 6,419,491 | B1 | 7/2002 | Ricci et al. |
| 6,482,444 | B1 | 11/2002 | Bellantone et al. |
| 6,497,573 | B2 | 12/2002 | Wagner et al. |
| 6,537,069 | B1 * | 3/2003 | Simmons, Jr. ............... 433/173 |
| 6,984,392 | B2 | 1/2006 | Bechert et al. |
| 7,338,286 | B2 | 3/2008 | Porter et al. |
| 7,484,959 | B2 | 2/2009 | Porter et al. |
| 7,491,058 | B2 | 2/2009 | Jorneus et al. |
| 7,780,446 | B2 | 8/2010 | Sanchez et al. |
| 7,906,132 | B2 | 3/2011 | Ziegler et al. |
| 8,033,826 | B2 | 10/2011 | Towse et al. |
| 8,043,091 | B2 | 10/2011 | Schmitt |
| 8,185,224 | B2 | 5/2012 | Powell et al. |
| 8,272,870 | B2 * | 9/2012 | Van Lierde et al. ............. 433/72 |
| 2004/0132603 | A1 | 7/2004 | Narhi et al. |
| 2006/0046229 | A1 * | 3/2006 | Teich ........................... 433/173 |
| 2007/0264612 | A1 * | 11/2007 | Mount ......................... 433/173 |

OTHER PUBLICATIONS

Areva, Sam, et al., "Use of sol-gel-derived titania coating for direct soft tissue attachment", Wiley InterScience, pub. www.interscience.wiley.com, Jun. 2, 2004.

Biomet 3i, ART953C PreFormance Brochure,"Rapid Adjustment. Enduring Strength. Aesthetic Design.", Feb. 2008.

Biomet 3i et al., ART1011A NanoTite Implant System Brochure, "NanoTitle Prevail Implants: Crestal Bone Preservation in the Aesthetic Zone", vol. 6, Issue 2, Jul. 2007.

Biomet 3i, ART1018 Provisional Components Brochure, "Your Patients Require Immediate Aesthetic Solutions . . . Biomet 3i Has Optimal Products", Jun. 2009.

Biomet 3i et al., ART1060 EncodeCP Brochure, "Provisionalization with Soft Tissue Sculpting Prior to Fabrication of a CAD/CAM Abutment", vol. 7, Issue 3, Jun. 2009.

Biomet 3i, Osseotite Implants, Restorative Manual, Dec. 2009.

Frojd, Victoria, et al., "Effect of Nanoporous $TiO_2$ Coating and Anodized Ca2 Modification of Titanium Surfaces on Early Microbial Biofilm Formation", BMC Oral Health, 2011.

Giordano, Russell, II, Compendium, Clinical Materials Review, "Zirconia: A Proven, Durable Ceramic for Esthetic Restorations", vol. 33, No. 1, Jan. 2012.

Kan, J,Y.K. et al., "Interimplant Papilla Preserv. in the Esthetic Zone: A Report of Six Consecutive Cases", The Int'l Jrnl of Perio. & Rest. Dentistry, vol. 23, No. 3, 2003.

Nevins, M. et al., "Histologic Evid. of a Connective Tissue Attachment to a Laser Microgrooved Abutments . . . ", The Int'l Jrnl of Perio. & Rest. Dentistry. vol. 30, No. 3, 2010.

Biomet 3i et al., PreFormance Temporary Cylinder Brochure, "Immediate Provisional Restoration of Implants with PreFormance Provisional Components", May 2007.

Perry, Ronald D., Compendium, Clinical Materials Review, "Provisional Materials: Key Components of Interim Fixed Restorations", Jan. 2012.

Kan, Joseph, Y.K., "Immediate Placement and Provisionalization of Maxillary Anterior Single Implants: A Surgical and Prosth. Rationale", Pract. Periodont Aesthet Dent, 2000.

Wohrle, Peter S., Single-Tooth Replacement in the Aesthetic Zone with Immediate Provisionalization: Fourteen Consecutive Case Reports, Pract Periodont Aesthet Dent, 1998.

* cited by examiner

SOFT-TISSUE PRESERVATION TEMPORARY (SHELL) IMMEDIATE-IMPLANT ABUTMENT METHOD AND DEVICE

FIELD AND BACKGROUND OF THE INVENTION

The present invention relates generally to the field of dental implants and, in particular, to a new and useful soft-tissue preservation abutment arrangement and method.

General Considerations and Problems to Overcome

The tooth is a structure of the oral cavity which is vital to the capability of chewing and important to the general well-being and appearance of people. Anatomically, the tooth resides within the oral cavity, firmly anchored within the upper and lower jaws (maxilla and mandible). Human teeth reside within two distinct anatomic regions of the jaws; the apical inferior portion of the tooth (the root) is connected to the jaw via an attachment called the periodontal ligament. We will here define this portion of the tooth that is connected to the bone as the "bone-zone" or hard tissue zone of the tooth. Second, the superior portion of the tooth (the anatomic crown) is connected to the jaw in the soft-tissue or gingival region of the jaw defined as the "tissue-zone" or soft tissue zone. The anatomic crown is demarcated as that portion of the tooth superior to crest of bone and it will include a small portion of the root superior to the crest of bone as well as the clinical crown that is visible. The tissue-zone forms a soft-tissue collar around the neck of a tooth. This tissue-zone connection (i.e. soft-tissue to tooth attachment) is composed of gingival fibers that insert into the superior aspect of the root surface; specifically, hemidesmosmal cell attachment to the root and crown forming a biological adhesion of the sulcular epithelium (gingival tissues) to the surface of a tooth.

The tissue-zone connection plays a critical role in maintaining health of the oral cavity. It does this by preventing the ingress of microbes and foreign substances into the body by providing a "biologic-seal" at the interface of the tooth-jaw connection at the tissue-zone. This functional attachment of the soft-tissue to the surface of the tooth should be fully appreciated as a critical defense barrier. As without the presence of this soft-tissue biologic seal the underlying bone would be vulnerable to numerous invasions of various foreign substances.

In addition, the tissue-zone plays an essential role in maintaining and preserving the dental esthetics of the smile. This same tissue-zone represents the peaks (papillae) and valleys of the soft-tissue gingival that surround the neck of each and every tooth. It is the spatial relationship of tooth form and color with healthy soft-tissue gingival architecture that are known as the essential building blocks of dental esthetics as we know it. Experts of dental esthetics have called the soft-tissue gingiva "the frame" of the picture, and regard the teeth as the "subject matter" of that painting. Disregarding the frame of a painting would certainly impact the overall esthetic appearance being viewed, and the same is true with respect to the gums and teeth. The loss or the alternation of anatomic structures of the tissue-zone has been shown to lead to an inferior esthetic outcome in addition to causing a potential risk of disease for the patient.

The tooth and its attachment to the jaw is subject to numerous pathogens over the lifetime of a patient, particularly due to trauma/fracture, endodontic failure, decay, localized periodontal disease, etc. Any of these conditions can lead to the eventual need for removal of either a single tooth or multiple teeth. The removal or extraction of a tooth or teeth will result in a radical morphologic change to the anatomy as well as the potential exposure of the internal tissues (connective tissues and underlying organs) of the body to invasion by foreign substances.

The extraction of a tooth results in a cascade of changes depending on how this procedure is performed. Tooth removal in the past has been a highly traumatic surgical procedure. It was not uncommon for an oral surgeon to fully reflect the gingival tissues as a surgical flap to expose the underlying tooth and bone to aid in the ease of access and visualization of the tooth to be removed. It is during this surgical reflection of the gingival soft-tissues that the normal anatomy of the tissue-zone would be radically altered and permanently changed. Destruction of the normal architecture of the gingiva occur as surgical instruments were used to cut, tear, crush and rip the attachment fibers between the tooth and soft-tissues of the tissue-zone. In accordance with gingival surgical flap surgery, closure of a surgical flap is accomplished with the placement of sutures to close the wound created. Primary (or complete) flap closure is highly desirable to ensure the re-establishment of a biologic-seal of the soft-tissue to prevent ingress of foreign bodies to the host.

Gingival flap surgery also has the known deficiency to result in bone loss from the stripping away of the periosteum and hence the blood supply to the bone during the reflection of a surgical flap. It is well documented in the dental literature that gingival surgical flaps result in bone loss by the exposure of the underlying bone. Dr. Lindhe and co-workers have scientifically demonstrated that surgical flap elevation and removal of teeth leads to loss of the residual bone and the shape of remaining ridge after tooth removal. These undesirable anatomic changes to the bone make the placement of implants more complex and increases risk for patients.

For the reasons identified above, the trend toward minimally invasive surgical procedures has been developed toward the extraction of teeth. Examples of these changes include the use of micro-surgical instruments, periotomes and extraction forceps that do not require the reflection of a surgical flap to remove teeth. Ultrasonic (piezo technology) surgical instruments, dental lasers and rotary devices have been suggested as mechanisms to minimize trauma during the removal of teeth. It is generally accepted within the profession that a minimally invasive technique for tooth removal should be the standard of care.

In an attempt to minimize detrimental anatomic changes during the surgical removal of a tooth, a major effort is now underway to preserve the bone-zone and tissue-zone after tooth removal. The objective of the dental profession to preserve bone was a natural extension of a vast body of knowledge recently created on periodontal bone regeneration via the use of bone replacement substances. Examples of such efforts include autografts, allografts, xenografts and a variety of bone replacement materials that include; Bone Morphogenic Proteins (BMP's), Stem Cell Derviatives, Platelate Rich Proteins (PRP's) derived from the blood and numerous other biologic sources. Bone regeneration after periodontal disease is well established in the prior art. A deficiency of using bone replacement substances, is the inability to contain and protect these materials to exposure to the oral cavity during the critical healing phase, i.e. a fundamental inability to re-establish the all-important biologic-seal of the Tissue-Zone once a tooth is removed.

The use of barrier membranes for guided tissue bone regeneration (GTR) is known attempts to preserve and regenerate lost bone after periodontal disease. The use of membranes has more recently been applied to the regeneration and preservation of bone after tooth removal. Barrier membranes assist in creating a protective barricade to the bone-zone by excluding unwanted cells (connective tissue cells) to the healing site. This is an attempt to allow the body to more effectively refill a residual bony socket with bone cells (a.k.a. osteoblasts) known to be critical for bone growth. A general deficiency of using barrier membranes is the direct exposure of a barrier membrane that consequently lends to the inability to establish a soft-tissue seal. The exposure of the barrier membrane leads to plaque accumulation on the surface of the membrane that is impossible to clean. Once membranes become exposed to the oral environment, bacteria colonization on the surface of the membrane quickly spearheads an infection and/or failure of regeneration of bone. The primary cause of the exposure of the membrane is a lack of a soft-tissue biologic-seal after gingival flap surgery. The inability to re-establish a biologic-seal after the removal of a tooth has many repercussions to bone and soft tissue regeneration.

Loss of the biologic-seal of the tissue-zone also has a significant impact on soft-tissue changes to both the macro- and micro-anatomy of the gingiva. It is accepted in the dental literature that the loss of gingival attachment within the tissue-zone leads to the irreversible loss of the interdental papillae and the gingival architecture surrounding a tooth. There are currently no predictable surgical techniques available to correct the gingival changes to vertical height and horizontal dimensional after tooth removal. Much effort has been directed toward preserving the bone after tooth removal but far less effort has been applied to preserving the macro- and micro-anatomy of the tissue-zone after tooth removal.

As will be explained more fully in the following, the new method and arrangement of the present invention is an effective means to preserve the esthetic and anatomic architecture of the tissue-zone after tooth removal and the immediate placement of a dental implant. In addition, the present invention simultaneously and effectively re-establishes the all-important biologic-seal after tooth removal and immediate implant placement.

The understanding of using a minimally invasive technique as well as re-establishing a biologic-seal after tooth removal has been discussed but has not yet been made possible in all cases by known methods and apparatuses. In addition to these important concepts one further concept related to tooth removal is the technique of immediate dental implant placement after the extraction of a tooth/teeth.

The replacement of a tooth by a dental implant device is well known in the prior art. It is understood that there are two basic components to the dental implant device; the root-form component held within the bone-zone commonly referred to as the "dental implant" and a second component, the implant anatomic crown composed of an abutment and clinical crown. Both the abutment and clinical crown are typically placed superior to the crest of bone therefore within and superior to the tissue-zone. An implant prosthesis was first described as a surgical method and device that used a fully submerged, non-loaded healing period prior to the connection of the dental implant crown.

The advent of contemporary implant dentistry was first described by Prof. P. I. Branemark in the late 1970's and established the use of a titanium root-form screw to be inserted into the bone placed by using an atraumatic surgical technique described by this researcher/inventor. The method described by Branemark discussed the placement of the dental implant into jawbone of a fully edentulous ridge. He described a method in which the implant would be fully submerged and non-loaded during a healing period of 4-6 months after the dental implant was placed and covered within the bone. Pre-operative conditions therefore required a fully healed ridge in which teeth were previously removed.

The method of using a submerged, non-loaded healing period for dental implants remains an approach still widely utilized today.

However, over the past 30 years alternative methods to implant placement have occurred. The following are different methods that have been advocated to the non-submerged, non-loaded implant healing technique.

Advantages and disadvantages will be briefly discussed for each technique.

Delayed, Submerged, Non-Loaded Implant Placement Method:

Defined as the method for placing a root-form dental implant into the jawbone. The implant is placed within the bone-zone initially. The pre-operative condition requires an edentulous ridge. The technique describes the placement of the implant into the bone at or below the crest of bone and it is fully covered by primary flap closure. An initial healing for a period of 4 to 6 months is required. A second surgery is required to expose the root-form implant and to connect a healing abutment. Second healing period of 2-3 months is required for soft-tissue. Final crown delivery occurs approximately 9 months after the start of treatment.

Deficiencies of this Method:

1. Requires multiple surgeries prior to implant crown placement.
2. Requires an edentulous ridge prior to implant placement into the bone-zone resulting in the irreversible changes to the soft-tissues of the tissue-zone.
3. Difficult to re-establish a biologic-seal after numerous surgeries and the connection of the implant crown.
4. Increased cost because of multiple surgeries and prosthetic components.

Delayed, Non-Submerged, Non-Loaded Implant Placement Method:

Defined as the method for placing a root-form dental implant into the jawbone exemplified by the Straumann, ITI implant company. The implant is placed within the bone-zone initially. The pre-operative condition requires an edentulous ridge. The technique describes the placement of the implant into the bone at or below the crest of bone or within the tissue-zone. A transmucosal healing cap component is used. A healing abutment or "cap" is placed onto the implant that is in direct contact with the soft-tissue during the initial bone-healing period of 4 to 6 months. A second surgery is not required to expose the root-form implant. Reformation of the tissue-zone is required. A connection between the implant and the healing abutment is within the tissue-zone.

Deficiencies of this Method:

1. Requires an edentulous ridge prior to implant placement into the bone resulting in the irreversible changes to the soft-tissues of the Tissue-Zone.
2. Requires flap surgery to place dental implant.
3. Difficult to re-establish a biologic-seal after surgery and the connection of the implant crown.
4. Difficult to re-establish soft-tissue anatomy to the state it was prior to tooth removal.
5. Healing abutment has an connection interface within the Tissue-Zone, which allows bacteria to adhere impeding wound healing.
6. Increased cost because of multiple components.

Immediate Root-Form Implant Placement:

A recent trend in implant dentistry that has occurred, that overcomes the deficiency of requiring multiple surgeries, is the immediate placement of a root-form dental implant directly into an extraction socket after tooth removal.

This method deviates from the original protocols established by Branemark and co-workers. The advantage to the simultaneous placement of a root-form dental implant after tooth removal is the reduction of the number of clinical procedures required as well as decreased treatment time. This technique eliminates the need to have the bone ridge healed after tooth removal consequently requiring fewer surgical procedures.

Immediate implant placement requires a mechanical locking of the root-form dental implant into the residual socket-site after a tooth has been removed. Mechanical locking refers to the root-form implant engaging undisturbed bone in an attempt to provide primary mechanical stability of the implant within the extraction socket. Immediate implant placement is highly desirable in comparison to delayed implant placement since it allows the immediate replacement of the tooth at a substantially reduced amount of time when compared to previous method of delayed implant healing.

Immediate Implant Placement Presents Numerous Risks and Deficiencies with Current Methods Used:

1. An inability to fully engage the entire remaining socket surface after tooth removal, thereby leaving a space (gap) between the surface of the implant and the surface of the remaining bone.

2. An inability to establish a biologic-seal to the overlying soft-tissues after a tooth has been removed.

3. An inability to retain bone regenerative materials if a residual gap remains between the surface of the implant and the bone socket.

4. An inability to establish a biologic-seal of the soft-tissue over a barrier membrane to protect and contain bone regeneration materials and the blood clot.

5. Inability to preserve the soft-tissue architecture of the gingival of the Tissue-Zone.

The deficiencies of achieving a predictable and esthetic long term outcome when using an immediate implant placement protocol can all be directly attributed to the inability to establish an acceptable biologic adaptation to create an effective biologic-seal in the tissue-zone of the remaining soft-tissue socket after removal of a tooth.

Immediate implant placement of a root-form dental implant has been shown to effectively osseointegrate by numerous authors (reference included herein). The residual gap that is present between the implant surface and the bone surface requires careful management whether a surgical flap is performed or a non-flapless minimally invasive extraction technique is used. In either of these two approaches, irreversible soft-tissue changes have been shown to occur with immediate implant placement after tooth removal. Changes within the tissue-zone are shown to occur as early as 2-3 days after the immediate implant placement.

OTHER PRIOR ART

U.S. Pat. No. 5,417,568 to Giglio discloses a dental prosthesis that is said to accommodate the gingival contours surrounding the implant prosthesis by imitating the gingival contours around natural teeth. Since the abutment is rigidly connected to the implant and must always be axially aligned with the long axis of the implant, the abutment will rarely, if ever, closely engage the entire existing soft-tissue socket created when a tooth has been extracted; consequently, inadequate soft tissue socket adaptation exists. Moreover, seldom is the axis of the implant exactly aligned with the axis of the soft-tissue socket. Also, although the abutment disclosed by this patent has raised ridges around its outer perimeter, it is symmetrical, and therefore does not mimic the asymmetric anatomy of a soft-tissue socket in the gingiva of a patient from whom a tooth has been extracted.

Nowhere in the prior art or in current dental implant wisdom is an anatomically shaped and sized abutment in the form of a hollow, asymmetric tubular shell used in conjunction with a dental implant, that is not rigidly or concentrically connected to the implant in advance. As a result of the invention here disclosed, the shell can be moved and maneuvered to any orientation in the x-, y- or z-axis in a soft-tissue socket to effectively and fully engage the tissue-zone with no space or gap between the outer surface of the shell and the soft-tissue socket, independent of the position and axial orientation of the implant in the bony socket. The mechanical de-coupling of the abutment shell from the implant is one of several important advancements of this invention over the prior art.

US RE37,227 to Brodbeck also disclosed a some-what anatomically shaped abutment but again it is axially fixed to an implant so that there is no freedom of movement between the abutment and the implant but rather they are mechanically coupled to each other when being seated in their respective soft-tissue and bone sockets.

An article titled: "*Immediate Placement and Pro visionalization of Maxillary Anterior Single Implants: A Surgical and Prosthodontic Rationale,*" by Kan at al., Pract Periodont Aesthet Dent, 2000; Vol. 12, No. 9, pps 817-824, discloses the building up of an abutment that is fixed to an implant to better match a soft-tissue socket by the addition of autopolymerizing acrylic resin around the abutment by sculpting the outer shape of the otherwise fixed abutment to better fill the soft-tissue socket. This technique also fails to recognize the advantage of mechanically decoupling the abutment from the implant. In addition, the tissue-zone collapses immediately upon tooth removal and extrapolation of its contours by the author is required to recreate as close as possible the soft tissue-zone profile.

Another attempt at accommodating the mis-match between an implant oriented in a bony socket and an abutment positioned in a soft-tissue socket, is suggested in the June 2009 brochure of BIOMET 3i titled "*Ideal Solutions For Immediate Aesthetics*" that discloses an abutment-implant combination where the abutment axis is at a fixed but non-aligned angle to the implant axis. Here again there is no decoupling of the abutment from the implant so freedom of orientation is not present.

SUMMARY OF THE INVENTION

It is an object of the present invention to solve the problems of the prior art by providing a soft-tissue preservation, dental implant arrangement, that comprises: a hollow shell with an interior volume and a shell axis, the hollow shell having an outer bio-compatible surface for engaging a soft-tissue socket that is left in gingival tissue after a tooth has been extracted from a bone socket under the gingival tissue, the shell having a first perimeter adapted for placement toward the bone socket and a second perimeter adapted for placement adjacent an outer surface of the gingival tissue around the soft-tissue socket, the first perimeter being smaller than the second perimeter so that the shell tapers outwardly from the first to the second perimeters, the second perimeter being asymmetrically scalloped with opposite distal and mesial peaks and opposite lingual and facial valleys between the peaks, and the shell being sized for closely engaging against the soft-tissue socket without gaps; a dental implant having an implant axis and being adapted for placement in the bone socket; a temporary post rigidly connected to and coaxial with the dental implant, the temporary post extending in the interior volume of the hollow shell; and a luting compound filling the interior volume between the shell and the temporary post and setting solid for fixing the shell to the dental implant with no other connection between the shell and the implant so that the outer surface of the shell engages against the soft-tissue socket without gaps and without requiring alignment of the shell axis to the implant axes.

A further and more general object of the invention is to provide a dental implant method and arrangement that uses a hollow shell with outer bio-compatible surface for engaging a soft-tissue socket that is left in gingival tissue after a tooth has been extracted to promote healing by mechanically decoupling the shell from an implant that has been fixed in the remaining bony socket, the shell being tapered outwardly from a first to a second perimeter, the second perimeter being asymmetrically scalloped with opposite distal and mesial peaks and opposite lingual and facial valleys between the peaks, the dental implant in the bone or bony socket left after tooth extraction being rigidly connected to a temporary post, the temporary post extending in the shell and a luting compound filling the volume between the shell and the post and setting solid for fixing the shell to the dental implant with no other connection between the shell and the implant so that the outer surface of the shell engages against the soft-tissue socket without gaps and without requiring alignment of the shell and implant axes.

Another objects of the invention are to use the shell as a biological seal for both the soft-tissue socket and for the bony socket, to preclude contaminants from the soft-tissue and from the bony sockets.

Another object of the invention is to use the shell as a foundation for a temporary prosthetic tooth for immediately cosmetically replacing an extracted tooth.

Other objects of the invention will become apparent after considering the following more detailed disclosure of the invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
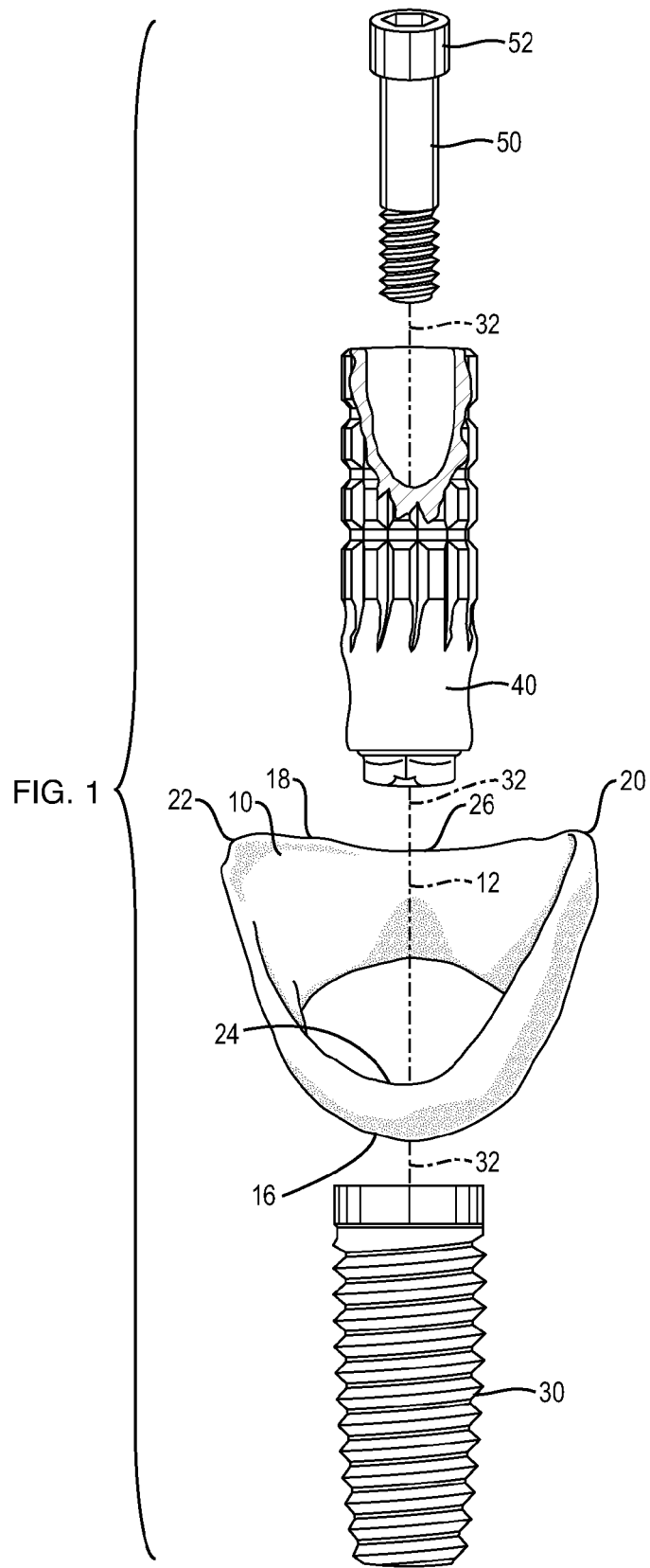
FIG. 1 is an exploded view of important part of the arrangement of the invention.

Apparatus and Arrangement of the Invention:

Referring now to the drawings, in which like reference numerals are used to refer to the same or similar elements, FIG. 1 illustrates a soft-tissue preservation, dental implant arrangement, that comprises a hollow shell 10 with an interior volume and a shell axis 12. The shell is advantageously made of zirconium dioxide ($ZrO_2$) ceramic material that is known to be bio-compatible. The hollow shell 10 thus has an outer bio-compatible surface for engaging a soft-tissue socket that is left in gingival tissue after a tooth has been extracted from a bone or bony socket under the gingival tissue. Shell 10 has a first lower perimeter 16 adapted for placement toward the bone socket of a lower mandibular, tooth. The first or inner perimeter 16 may be an upper perimeter if the shell is to be used for replacing of an extracted upper or maxillary tooth so that terms like "upper" and "lower" as used here are only relative terms and do not convey an absolute position or limitation of the invention.

Shell 10 also has a second or outer perimeter 18 adapted for placement adjacent an outer surface of the gingival tissue, around the soft-tissue socket. The first perimeter 16 is smaller than the second perimeter 18 so that the shell 10 tapers outwardly from the first to the second perimeters to anatomically mimic the shape of the soft-tissue socket that remains immediately after a tooth has been extracted, and before the soft-tissue socket starts to shrink or shift from the natural size, shape and position it had around the patient's natural tooth before extraction.

To further anatomically mimic the shape of the soft-tissue socket, the second perimeter 18 is also asymmetrically scalloped with opposite distal and mesial peaks 20 and 22, and opposite lingual and facial valleys 24 and 26, between the peaks. The shapes, sizes, locations and heights of the peaks and valleys are selected to mimic known tooth types, e.g. maxillary or mandibular, central or lateral incisors, canines, premolars and molars, and the shell is also sized for closely engaging against the soft-tissue socket without gaps of many tooth shapes, types and sizes. This sizing and shaping is achieved by providing the practitioner with a set or selection of different shell shapes, sizes and types, so that a shell 10 that is close in fit to the soft-tissue socket is available, so that the shell engages the soft-tissue socket without gaps and thus forms a biological or biologic-seal to preclude contaminants from the soft-tissue socket and from the bony socket in the bone under the soft tissue.

As will be explained more fully in the following, the present invention allows this placement of the properly sized and shaped shell 10, in the soft-tissue socket, with complete freedom of motion in the x-, y- and z-directions and, just as importantly, with complete freedom of rotation about all three axes. This is done by mechanically de-coupling the abutment that is formed by this shell and the post 10, from the solid implant that must be rigidly fixed in the bony socket at its own optimum angle and depth.

A dental implant 30 having an implant axis 32 is provided and is adapted for placement in the bone socket immediate after tooth extraction, clearing and dressing of the bony socket in a conventional manner, for example, by removing debris and drilling an immediate implant receiving bore in the bone or bony socket using known techniques.

A temporary post 40 is then rigidly connected to and is coaxial with the dental implant 30, for example, by using a screw 50 that is inserted into a central bore in the post 40 and screwed into a treaded bore in the top center of the implant 30. A head 52 engages an annular step in the post 40 in a known manner, to fix the post 40 to the implant 30. The temporary post 40 extends in the interior volume of the hollow shell 10 but is not yet connected to the shell, and need not even touch the shell, so that despite the fixing of the post to the implant, the shell can be engages to the soft-tissue socket without directional or rotational limitation.

Figure 6:
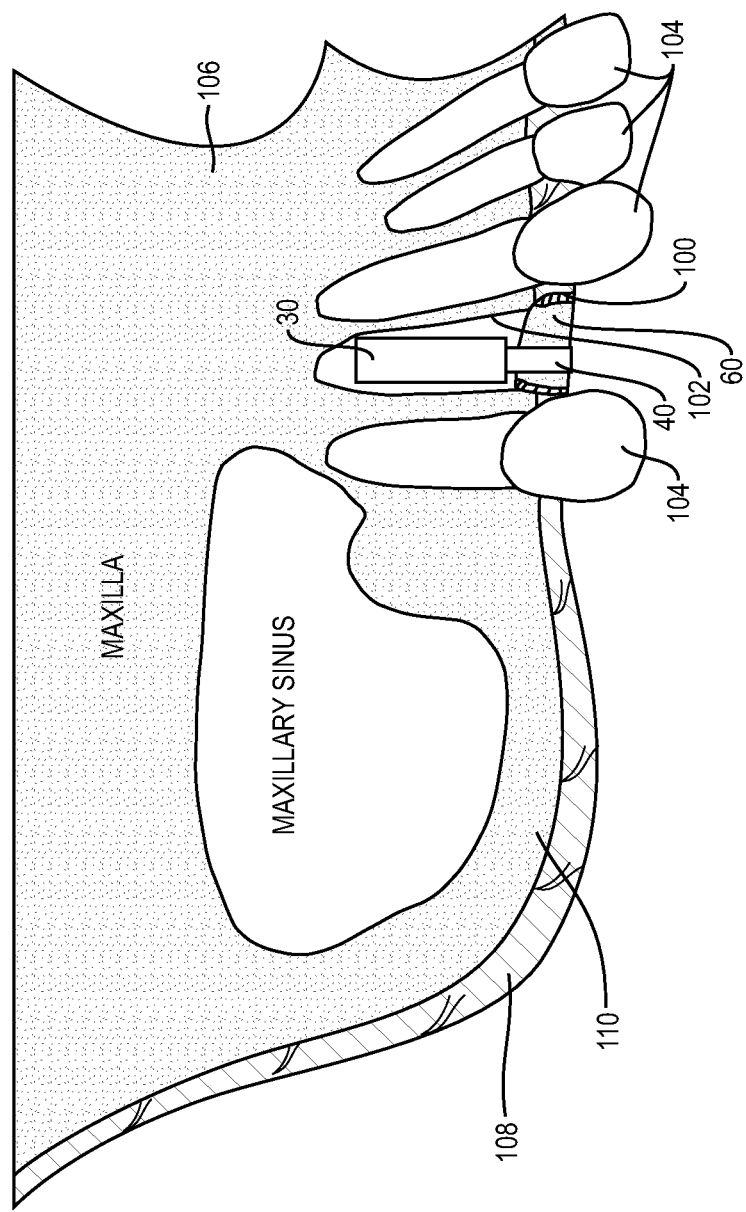
FIG. 6 is a sectional view of the arrangement of the invention after a luting compound has been applied.
Figure 8:
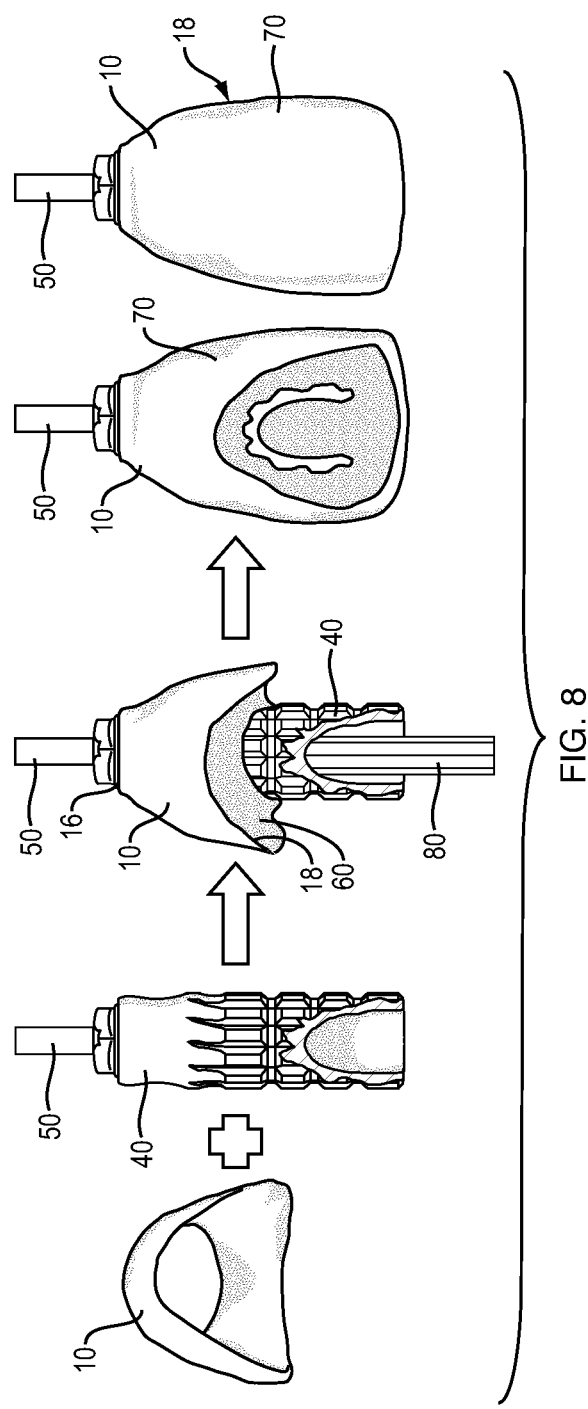
FIG. 8 is a composite view of parts of the arrangement of the invention in a sequence showing an assembly of the parts of the arrangement.

An initially fluid luting compound shown at 60 in FIGS. 6 and 8, is filled into the interior volume between the shell 10 and the temporary post 40 and is allowed to set solid. Only then is the shell 10 fixed to the dental post 40 and implant 30, with no other previous connection between the shell and the implant so that the outer surface of the shell engages against the soft-tissue socket 100 without gaps and without requiring any alignment between the shell axis 12 and the implant axes 32. This also seals the bony socket 102 in the jaw bone 106, which, in the case of FIG. 6, is the maxilla that is shown to have other teeth 104 on opposite sides of the extracted tooth socket 102. The inner surface of shell 10 is adapted to adhere well to the luting compound 60. This is done by making the shell, and therefore its inner surface, of a material that adheres well to the luting compound, e.g. zirconia, or by treating the inner surface, e.g. by roughening its texture, or by applying a special coating to the inner surface that adheres well to the shell material and to the luting compound when the compound hardens.

Figure 3:
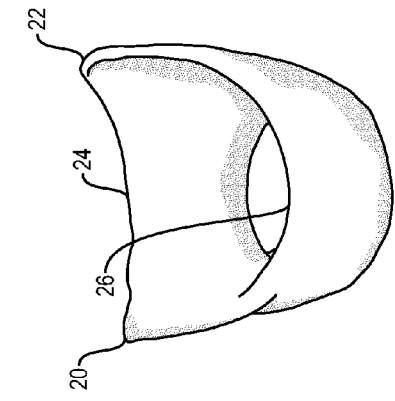
FIG. 3 is a perspective view of a still further embodiment of the shell of the invention for use in replacing a different tooth type.
Figure 5:
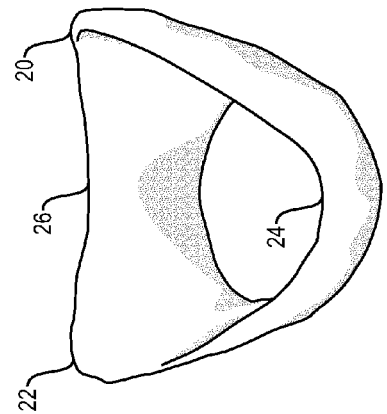
FIG. 5 is a perspective view of the shell of the invention shown also in FIG. 1 for comparison with the shell shapes of FIGS. 2 to 4.
Figure 2:
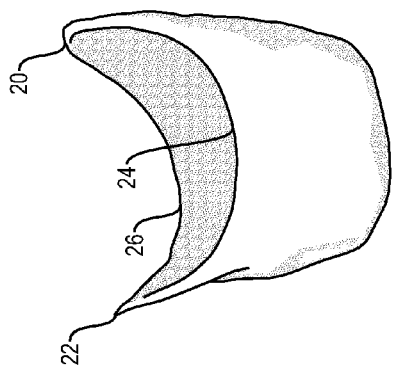
FIG. 2 is a perspective view of a different embodiment of the shell of the invention for use in replacing a different tooth type.
Figure 4:
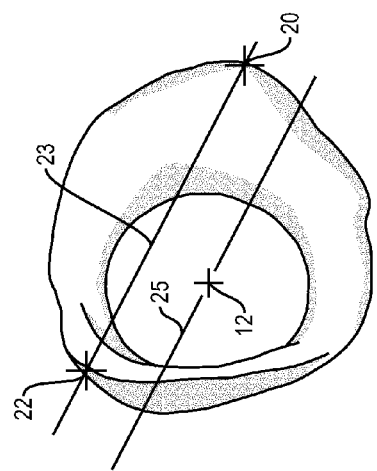
FIG. 4 is a perspective view of an embodiment of the shell of the invention that illustrated the asymmetry of the outer perimeter of the shell.

As illustrated in FIGS. 1 and 5, the lingual valley 24 is lower than the facial valley 26 for mimicking maxillary and mandibular incisors for example. For mimicking maxillary and mandibular canines, the valleys 24 and 26 can be of substantially equal in height as illustrated in FIG. 2. For premolars and molars, the opposite of incisors is true so that as shown in FIG. 3 the lingual valley 26 is higher than the facial valley 24 and mesial and distal peeks 20 and 22 are not as highly scalloped as in incisors. Also for some or perhaps most tooth types, the distal and mesial peaks 20 and 22, as shown in FIG. 4, are not in a common plane 23 with the plane 25 extending through the shell axis 12. The asymmetry is also selected to more closely mimic the true shape and size of a soft-tissue socket before it starts to deteriorate. These rules are not absolute since there can always be exceptions and variations to the rules because dental anatomy varies and may sometimes reside outside the norms. The set of shell in various sizes, types and shapes provided to the practitioner can accommodate to these variations by allowing the practitioner to select a shell for a different tooth replacement type or, in extreme cases, may arrange for a custom made shell for a particular patient.

Other parts that may be included as part of the arrangement of the invention to be explained later in this disclosure, include a tooth form temporary 70 in FIG. 7, that can be fixed to the outer perimeter 18 of the shell 10, after it has been luted to the post 40, so that the patient has a temporary tooth replacement before leaving the dental office. The arrangement may also includes a cylindrical nylon plug 80 in FIG. 8, that is used to temporary plug the interior volume of the post 40 above the securing screw 50, before the luting step, so that access to the head 52 of the screw 50 can be reestablished when a permanent tooth replacement is to be attached to the implant, or at other points in the process of the invention, by extracting the plug.

Methods and Procedures of the Invention:

With reference to FIGS. 6 and 8, the method of the invention permits immediate implant soft-tissue abutment temporary placement at the time of tooth extraction to re-establish an effective biologic-seal of the soft-tissues to the surface of the abutment or shell more effectively to its anatomic shape.

The immediate implant soft-tissue abutment temporary may be:

1. An immediate soft-tissue implant abutment temporary extending from the crest of bone 110 to the height of the remaining soft tissues 108. The immediate soft-tissue abutment temporary will re-establish a biologic-seal preserving the gingival soft tissues after the removal of a tooth and the immediate placement of an implant. It also enables containment of bone regenerative materials and primary coverage of the barrier membrane if used after tooth removal; and/or 2. An immediate tooth-form implant temporarily re-establishes a biologic-seal preserving the gingival soft tissues after the removal of a tooth and the immediate placement of an implant. It also enables containment of bone regenerative materials and primary coverage of the barrier membrane if used after tooth removal.

The immediate implant soft-tissue abutment temporary is a temporary component that connects to the implant-platform (superior surface of the implant platform) at the bone crest 110 and extends to the level of the free-gingival margin of the soft tissue 108. It provides the necessary shape and adaptation to re-establish a biologic-seal between the soft-tissues and the surface of the temporary.

The immediate implant soft-tissue abutment temporary, i.e. shell 10, method has the following features or steps:

1. The method and device in the preferred embodiment use a surgically sterile surface for shell 10 with a bi-layer microtexture to promote immediate soft-tissue repair and adaptation promoting re-attachment or repair to the biologic surface. It is anticipated that the surface may have a regular microgeometric pattern that is uniform. It is also anticipated that the surface texture may be modified chairside using a rotary instrument such as a uniquely designed dental bur, that results in a ordered microgeometric repetitive surface pattern in the form of alternating ridges and grooves, each having an unfixed width in a alternating range of about 2.0 to about 25 microns (micrometers) and a nonfixed or altering depth in a range of about 10 microns to about 50 microns, in which the microgeometric repetitive patterns define a guide soft-tissue preservation and re-attachment of soft tissue fibers to the surface of the immediate implant soft-tissue temporary abutment.

2. The shell is hollow and is of generally tubular design to accommodate the position of an immediate root-form implant 30 positioned at multiple locations within the residual socket 102.

3. The method and device provides an immediate mechanical seal between the residual soft tissue socket and the surface of the immediate implant soft-tissue temporary (Provisional) abutment.

4. The method and device promotes cellular soft-tissue adherence to the surface of the immediate implant soft-tissue temporary (Provisional) abutment.

5. The method and device preserves the soft-tissue architecture of the gingival surrounding the immediate implant soft-tissue temporary (Provisional) abutment.

6. The method and device enables bone regenerative materials to be retained in any gap left around the top of the implant 30, and protected during initial healing but the shell, in effect, sealing this area from the outer end of the soft and bony sockets.

Figure 7:
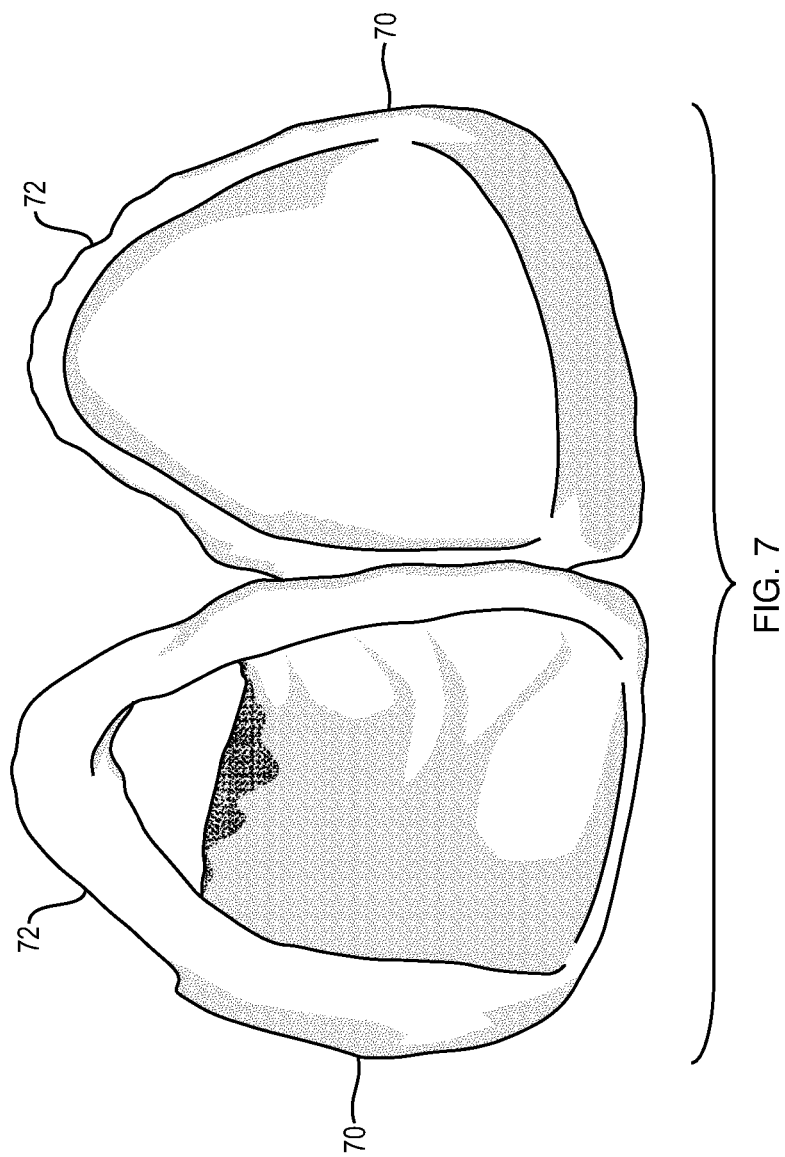
FIG. 7 is a composite, side-by-side, rear (lingual) and front (facial) perspective view of an immediate tooth-form temporary of the invention.

An immediate tooth-form temporary (provisional) 70 of the invention is shown in FIG. 7 and is a temporary component who's subgingival transmucosal section 72 is shaped similar to a root surface and represents the immediate transmucosal temporary (Provisional) described above and who's supragingival component is shaped like a tooth. It is composed of a shell 70 that extends from the implant-platform of the invention that includes the luted shell 10, and extends from the outer perimeter 18 of shell 10 beyond the level of the free-gingival margin to the incisal edge or occlusal surface of the dental tooth it is replacing. Tooth form 70 comes in a variety of different vertical heights, elliptical shapes and different dimensions to temporally replace the various types of teeth that might be extracted. It will be provided to dentist as a kit in which a variety of different sizes, shapes and types are available to replace different teeth that are extracted.

Critical to the design is creating an effective biological socket-seal between the surface of the abutment-temporary (provisional) to adequately support and seal the residual soft tissue socket at the time of placement. The subgingival shape of the abutment-temporary (provisional) promotes biological socket seal by providing either an over-contoured or under-contoured emergence profile to compensate for the position of the dental implant.

Additionally, the abutment-temporary design provides a single uniform material within the soft tissue zone of the residual soft tissue socket that prevents a micro- and macroscopic gap between dissimilar materials in the soft tissue gingival zone.

The abutment-temporary subgingival emergence profile provides an over-contoured or under-contoured shape that is anatomical to compensate for the three dimensional position of the underlying endosseous implant spatial position.

The abutment-temporary dental implant prosthesis is designed to be an interim prosthesis that is fabricated chairside and is customized to provide individual unique tooth replacements. The temporary shell is designed from a series of elliptical and asymmetric shapes that have an eccentric opening for access to accept a cylindrical component that is attached via a screw mounting to the dental implant.

A self-curing material is used to affix the shell to a screw-retained temporary post 40 during the chairside fabrication of the abutment-temporary. The abutment-temporary (provisional) is modified chairside to generate a unique final shape and provide an adequate seal between the abutment-temporary (provisional) and the soft tissue socket. Preformed non-concentric elliptical shells provide a matrix to fabricate the abutment-temporary dental implant restoration.

The immediate abutment-temporary, that can also be thought of as an immediate provisional abutment, has one interface region between the dental implant and the overlying abutment-temporary. The interface is at the level of the implant buccal plate and contained at the level of bone crest. This eliminates the micro- and macroscopic gap from being positioned within the soft tissue zone of the soft tissue residual socket for immediate implant placement into a fresh extraction site.

Description of Methods:

It is understood in the description of the method and device that the placement of an immediate soft-tissue preservation implant abutment has the intended use for the extraction and replacement of a single tooth or multiple teeth. The method will describe for a single tooth, but it is understood that the deception of the method and device is note limited to a singular tooth but implies a description for multiple teeth as additional embodiments of the invention. With reference to FIGS. 6 and 8, a preferred embodiment of the method of the invention is hereafter described.

1. The diagnosis that a tooth requires extraction is determined by the dental clinician. The diagnosis is preformed using conventional means including clinical examination, radiographic analysis, detailed past dental history and the review of signs and symptoms. The patient is informed of the treatment alternatives and an appropriate informed consent to treatment is provided to the clinician.

2. Prior to the extraction of the tooth a clinical photo can be taken to allow future comparison of the pre-treatment condition that was present versus the post-operative outcome after treatment is completed. The photo may have a reference measurement tool or instrument so that detailed analysis of the soft-tissue changes can be analyzed.

3. A Dental impression either using conventional impression materials such as alginate, polyether, vinyl polysiloxane, and other materials to establish a accurate representation of the teeth and surrounding gingival tissues. It is understood that the described embodiment may also be performed using a digital impression such as cone beam computer tomography or digital oral impression (CAD/CAM Digital Impressions) using a hand-held oral scanning device of known design.

4. The area of the mouth in which the tooth is to be extracted is anesthetized with a dental local anesthetic solution. A local anesthetic solution is can be delivered to the area either as local infiltration dental injection or as a regional nerve block to the area. The patient is given adequate time (typically 5 minutes) for the dental local anesthetic to anesthetize the region of the mouth that is being treated.

5. Extreme care is used to preserve the entire tissue-zone and minimize trauma to the supporting gingival tissues 106 during each phase of treatment. It is critical to preserve the soft-tissue architecture of the immediate and surrounding gingival in order to re-establish the biologic-seal after the tooth is removed and the immediate soft-tissue implant abutment, i.e. shell 10, is placed. Therefore a flapless surgical technique is used.

a. The first step to performing this method is to carefully incise the entire supra-crestal attachment of the tooth 360 degrees around the tooth, i.e. around soft-tissue socket 100. It is important to surgically disconnect the soft-tissue attachment fibers. This can be accomplished using a surgical blade, piezo-surgical instrument, micro-rotary dental handpiece or dental laser soft-tissue cutting instrument. The method requires careful dissection of the supra-crestal attachment which includes the sucular epithelium, junctional epithelium, connective tissue inserting fibers which are found between the connective tissue and the surface of the root above the crest of bone. Once the supra-crestal fibers are released the superior periodontal ligament fibers (attachment fibers found between the alveolar bone socket and root surface) can next be incised.

b. The superior periodontal fibers attach the surface of the tooth (cementum) to the inner bony socket must also be severed using minimal disruption to the surrounding soft-tissue and bony architecture. This can be accomplished by using micro-surgical instruments, periotomes, a rotary diamond pointed diamond, piezo-surgical instrument, laser. It is important that the instrument diameter is between approximately 20 microns to 50 microns (or ⅛ to ¼ millimeter in diameter) as this is the dimension of the width of the periodontal ligament space. The surgical instrument is placed into the entrance of the periodontal ligament between the tooth 104 and inner socket wall 100. The periodontal attachment fibers are served around the tooth to a depth of 1 to 4 millimeters, depending on ease of entry into the periodontal ligament space.

c. The extraction of the tooth is first initiated using a rotational movement in order to sever the remaining subcrestal periodontal fibers attaching the tooth to the inner socket wall. This can be performed with either using a reduced diameter elevator, periotome or extraction forceps. Once a rotational movement is achieved a vertical force can be applied to the tooth to advance the root out of the bony socket 102.

When the extraction is performed using this method minimal disruption can occur to the surrounding soft-tissues of the gingival. The interdental papillae are not surgically altered from the pre-treatment condition. Incisors are not made which compromise the blood supply to the region of the bone or surrounding soft-tissue gingival. The architecture of the soft-tissue has not be altered other than the severing of the attachment fibers between the root surface and inserting fibers.

6. Removal of any inflammatory granulation tissue within the bony socket may be necessary. This is performed using a small sized circular curette. Inspection is performed to ensure the integrity of the remaining inner socket walls 100. A radiograph may be taken to determine the remaining configuration of the tooth socket. This step is referred to here as preparing the bony or bone socket.

7. Immediate insertion of dental implant 30 is performed. A dental implant is immediately placed within the residual extraction socket 102. The term "immediately" as used here means that the implant is placed shortly after the bony socket has been fully prepared to receive the implant, 10 to 30 minutes for example, but importantly during the same patient's visit.

a. The vertical position of the implant: The implant 30 can be placed at the level of the remaining crest of bone 110. Since the remaining crest of bone has different heights the implant may be slightly supra-crestal as one region and slightly sub-crestal at another region of the socket, this is to be expected.

b. The horizontal position of the implant: The implant is to be ideally placed with the axial position allowing for a screw-retained temporary. The center axis of the implant must therefore be placed in the position of the cingulum of the adjacent teeth; i.e., positioning the implant toward the palatal (lingual) aspect of the residual extraction socket 102. It is noted that the implant 30 will not be placed in the center of the socket 102 as this would result in the retention screw of the immediate-temporary to exit through the incisal edge of the tooth and will result in an esthetic compromise of the restoration. Positioning the implant biased toward the palatal (lingual) position of the extraction socket is critical so that a screw-retained immediate temporary restoration can be used. This advantageous placement of the implant is made possible by the fact that the abutment or shell 10 of the invention is mechanically de-coupled from the implant and need not be affixed with respect to the axis or position of the implant as has been common in the past. The preferred embodiment of the invention is an immediate screw-retained temporary to eliminate the need for cementation of the temporary. Retention of the immediate temporary relies upon mechanical retention of the screw. It is anticipated that the immediate temporary could be designed in with a temporary design in which it is cemented to the substructure directly and places the location of the micro gap below the soft tissue zone.

c. The immediate implant 30 must mechanically engage and lock into a portion of the remaining bone. This may be achieved at the apical end of the implant. It may also be achieved on a lateral portion of the surface of the implant.

It is understood that the implant diameter will be smaller then the greatest diameter of the root of the tooth that was removed. Therefore the dissimilar diameters between the immediate implant and the residual bony tooth socket must result in a "gap" or space between the residual bony socket 102 and the surface of the implant 30 as shown, for example in FIG. 6. Filling the entire tooth socket 102 is not desirable, as this method relies upon a residual gap between the facial surface of the immediate implant and the remaining buccal plate of bone. This gap will then allow for the placement of a bone regenerative material to be placed between the implant surface and the inner tooth socket buccal plate. The gap allows for future bone regeneration via the in growth of the blood supply and new osteoblasts. It is important not to use a implant diameter that would make direct contact to the labial plate of bone as this would compromise the blood supply that is needed to preserve the labial (buccal) plate of bone as the implant surface provide no ability for angiogenesis. This is critical point to appreciate and understand. The preservation of the overlying gingival and surrounding soft-tissues is preserved by several critical factors: (1) a minimally invasive surgical approach; (2) preservation soft-tissue architecture; and (3) preservation and promotion to re-establish the blood supply to the surrounding tissues.

8. Placement of the immediate soft-tissue implant preservation abutment shell 10: A screw-retained temporary post 40, such as the PreFormance Post from Biomet 3i Dental Implants of Palm Beach Gardens, Fla., is connected to the dental implant 30 held within the bone 102. The immediate soft-tissue abutment shell 10 is selected for the proper vertical and horizontal dimensions. The immediate soft-tissue preservation abutment shell 10, as noted above, is supplied in different dimensions depending upon the tooth to be replaced. It will have series of defined dimensions externally. These dimensions will includes a series of different tissue-zone heights ranging from 2 mm to 5 mm. It will be provided in several root form configurations and be provide in more then one horizontal widths. An example of the horizontal dimensions could be, but not limited to:

Maxillary Right Central Incisor:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.
Maxillary Right Lateral Central Incisor:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone
Maxillary Right Canine:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.
Maxillary Left Central Incisor:

Height 2 mm, Height 3 mm, thru 5 mm.
P Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.
Maxillary Left Lateral Central Incisor:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.
Maxillary Left Canine:
Height 2 mm, Height 3 mm, thru 5 mm.
Diameter, Small, Medium and Large.
An irregular superior surface is provided to conform to the soft-tissue gingival architecture. The interproximal points will be longer in dimensions then the labial and lingual surfaces.
The inner shell allows for the eccentric position of the shell over the center axis of the implant held within the bone.

It is understood that each shells 10 can be for the specific tooth being replaced. The dimensions of the shell are based on measurements of numerous soft-tissue sockets remaining after tooth removal. The shell 10 has the requirement to enable a soft-tissue socket-seal to be re-established. This is predicated upon allowing the proper dimensions to completely fill the soft-tissue (tissue-zone) socket 100.

In general terms and from observation of stone casts and extracted teeth as well as descriptions, pictures and illustrations in Dental Anatomy book, it seems that the "lingual valleys" are lower than "facial valleys" in maxillary and mandibular incisors. Max. and mand. canines "valleys" are of about equal height. Max. and mand. premolars and molars seem the opposite of incisors where "lingual valleys" are higher than "facial valleys" and mesial and distal peeks are not as highly scalloped as in incisors. Of course there are always exceptions and slight variations to the rule since each person dental anatomy will vary.

9. The preferred embodiment of the immediate soft-tissue implant preservation abutment shell is generally defined as a "tubular shell" which is open at both ends at perimeters 16 and 18. The inferior is placed into the soft-tissue socket 100 to make direct contact with the implant head platform of the implant 30 within bone 106. The superior surface is to approximate the free-gingival margin of the surrounding tissue-zone. The outer surface of the shell 10 is to make direct contact with the inner soft-tissue residual socket 100. The final adapted shell eliminates all openings and gaps between the soft-tissue socket and surrounding gingival. This re-establishes a biologic-seal to the underlying tissues below the surface. This will also provide containment and protection of any bone regenerative materials that are placed between the surface of the bone socket and the surface of the implant filling the "gap" between the dissimilar diameter of these two structures. If necessary a membrane can be placed at the level of the bony crest and placement of the shell 10 will provide complete coverage of the membrane below providing a biologic-seal to the outer oral environment. Once the shell is filled (see step 10 below) and modified it will also provide structural support to the soft-tissue gingival to prevent and preserve the architecture. The surface of the immediate abutment shell promotes soft-tissue adhesion to the surface. Allowing the superficial layers of the dermis to adhere to a smooth superior region of the abutment shell as well as encouraging functional fiber orientation to the roughened inferior region to promote a functional connective tissue attachment.

10. Luting (chair-side connection) of the immediate soft-tissue implant preservation abutment shell to the retaining screw-post of the implant: Once the proper abutment shell is selected from the variety of sizes and diameters it is placed within the tissue-zone soft-tissue socket. It is eccentrically positioned to the implant as previously described so that the outer surface of the shell make physical contact ensuring a biologic-seal between soft-tissue and surface of the shell. It is luted or connected to the screw-post in this position by using a chairside technique. The technique of connecting the shell 10 to the screw-post 40 can be performed with a variety of materials 60, in the preferred embodiment a cold-cure acrylic is used, in additional embodiments any number of polymerization materials can be used but not limited to composite, acrylic, resin, etc. The entire internal surface of the shell 10 is filled with luting compound as shown in FIGS. 6 and 8, eliminating voids or gaps within the material.

a. The superior surface can be filled to the level of the free gingival margin. An access hole will remain to allow removal of the shell, e.g. but inserting a nylon plug 80 into the central hole of the post 40 as shown in FIG. 8, for final finishing and temporary insertion.

b. The inferior surface is modified and any gap or voids are filled chair-side and then re-surfaced as described below.

11. Re-surfacing of the shell material, preparation and handling: In certain situations it may be necessary to modify the shape and surface of the shell 10 to properly adapt to the soft tissue socket 100. An additive technique of material or subtractive technique can be required in which additional materials or added or removed. To resurface the modified outer shell a novel surface texture bur is attached to a standard rotary handpiece. This preservation abutment shell bur is designed to re-establish the surface texture that was created in the texture zone on the outer surface of the abutment shell. A second step of cleaning is then required to ensure removal of all contaminants. This second surface cleaning step is accomplished by thorough cleaning, in the preferred embodiment this can require high-pressure, high-heat steam cleaning in alternative embodiments it is anticipated that autoclave, anti-microbial cleaning solutions may be applied to the surface to detoxify the contaminated surface.

12. After filling and reshaping of the shell 10 is completed it is removed from the implant by un-screwing the retaining screw 50. The abutment shell is then cleaned and inspected and all voids are filled and re-surfaced and cleaned as described above.

13. Placement of a standard cylindrical healing abutment is attached to the plate-form. The standard cylindrical healing abutment may be composed of titanium, stainless steel, anodized metal or other metal. It is conceivable that the standard cylindrical healing abutment is made from a cost saving polymer and disposed of after removal as this component is to be used as an intra-operative space maintaining during the placement of bone regenerative materials during this method. The standard healing abutment is selected to attach to the implant resulting with a noticeable gap between the outer surface of the standard cylindrical healing abutment and the soft-tissue socket. Bone grafting materials are placed within the gap between the bony socket 102 and surface of the implant 30 at or below the crest of bone. An optional barrier membrane can be positioned if necessary before or after the bone grafting materials being put into placed.

14. The standard cylindrical healing abutment is removed and discarded and the contoured refinished abutment inserted. In the preferred embodiment the retaining screw is put into placed and applying a seating torque to the screw that is between 15 newton-centimeters to 35 newton-centimeters.

15. The abutment shell 10 is adjusted to ensure that it is not in occlusal contact with the opposing teeth 104 when the patient closes their mouth.

16. A final radiograph is taken to assess the fit and position of the implant and shell.

17. The abutment shell 10 creates a biologic-seal to the underlying soft tissue and preserve the integrity of the surrounding gingival architecture. The abutment shell 10 is not to be removed for a minimum of 3-4 months at which time the fabrication of the final prosthesis can be initiated.

Further Structural Details of the Invention:

As noted, illustrated and described above, abutment shell 10 in its preferred form, is generally a tubular shell which is open at both ends. The tubular shell has the following specifications but it is anticipated that it may also have other designs features:

a. The shell is an irregular tubular design that mimics the shape of residual soft-tissue (tissue-zone) socket 102 that remains after a tooth has been removed. Examples of these shapes (generally occlusal views) are provided in FIGS. 2-5. The shape may more closely mimic the cross-sectional outline of a root in the tissue-zone region, but may also be designed to over-compensate on one or more surfaces to ensure physical contact along all aspects of the soft-tissue tooth socket. It is critical that the shell's fit with contact and not be causes excessive contact pressure at any specific point or area of the soft-tissue socket.

b. Outline shape of the two ends of the preservation abutment shell 10 is irregular as also illustrated in the drawings. The superior (gingival) surface of the shell (at outer perimeter 18) has a larger area when compared to the inferior (implant) surface (at inner perimeter 16) that comes into contact with the platform head of the implant 30.

c. The vertical height of the tubular shell will not be uniform. The interproximal surfaces at peaks 20 and 22 have a greater height when compared to the buccal and lingual surfaces at 24 and 26 of the tubular shell 10.

d. The emergence profile of the shell is one that has a variety of profiles to compensate for the position of the implant within the residual socket. Since the implant is to be intentionally placed off-center from the extracted tooth, the shell is intentionally placed eccentric to the immediate implant 30, placed within the bone. The shell is designed to be placed eccentric to the implant head. The emergence profile of the shell is over-compensated and under-compensated in the profile design allowing for the position of the implant. The compensating emergence profile design and ability to place the shell eccentric enables the re-establishment of an effective biologic-seal between the outer surface of the shell and the residual soft-tissue perimeter. The shell can be confined to the transmucosal (tissue-zone) region extending from the crest of bone to the free gingival margin or it may continue to extend into the oral cavity as the labial surface of material to replace the labial surface of the removed tooth in addition to the transmucosal region.

e. Surface Texture of Shell—In the preferred embodiment the outer surface text design can possess two distinct surface texture regions. The superior (gingival) surface region can be smooth to discourage the accumulation of plaque. The superior smooth zone may extend 1 mm to 3 mm. The inferior region will possess an ordered microgeometric repetitive surface texture or pattern. The inferior textured region covers the remaining outer surface. This textured surface encourages the re-establishment of the gingival fibers to make contact and adhere to the surface of the temporary abutment. The surface texture is not limited to two or more texture patterns, it is conceivable that the surface of the shell be design with a single texture covering the entire surface or designed from multiple textures to encourage direct soft-tissue adaptation within the tissue-zone. A smooth surface at the superior regions discourages plaque accumulation while the textured surface promotes and accelerates effective soft-tissue adhesion. The surface design discussed in the preferred embodiment has been shown to promote soft-tissue preservation in combination with providing an effective biologic-seal of the surface of the shell to the residual soft tissues.

f. Material—the shell can be composed of a variety of biocompatible materials including but not limited to; ceramic, acrylic, porcelain, lithium disilicate, zirconia and other crystalline structure. It is anticipated that this material can be composed of materials that are anti-microbial, bacteriostatic to retard the growth or colonization of the surface and internal surfaces with micro-organisms. Examples of such materials include but are not limited to; silver, copper, magnesium, titanium, hydroxyapitite, etc. These materials can be incorporated into the shell material or may be applied to the shell surface forming a second layer.

g. The connection interface between the abutment shell is placed at the level the implant head platform. In the preferred embodiment there is a single interface at the implant plateform at the bone crest level. This interface is a mechanical connection to minimize the placement of a micro- or macro-connection gap within the tissue-zone. The preferred embodiment is screw-retained. It is anticipated that a cementable version of the Immediate soft-tissue implant preservation abutment shell can be fabricated.

h. The preferred embodiment of the shell is confined to the tissue-zone, but it is anticipated that a second design could include part of all of the tooth form that was extracted.

As shown in FIG. 8, the tooth-form temporary 70 that is selected or created to match the extracted tooth, is then luted to the outer perimeter 18 of shell 10 so that the patient leaves with a cosmetically equivalent tooth replacement to the one extracted.

Disposable Standard Cylindrical Implant Intra-operative Abutment: This component is used as intra-operative abutment that is placed during the immediate soft-tissue implant preservation protocol to allowing bone grating materials to be placed within the bone gap between the implant surface and the bony residual socket. It also has the function to prevent bone grafting materials from entering into the internal screw hole of the implant prior to the placement of the immediate soft-tissue implant preservation abutment. It is a single use, disposable component. It can be fabricated from a variety of materials and come in a variety of heights and widths. The preferred embodiment is an inexpensive polymer material allowing it to be screwed or press-fitted into place during the placement of the bone grafting materials.

Immediate Soft-Tissue Abutment Texturing Bur: This component is a rotary bur that is designed to provide a micro-geometric repetitive surface pattern forming a varying widths and varying depths ranging from 10 microns to about 50 microns. The irregular repetitive pattern is created using a chair-side rotary instrument on the surface of the immediate soft-tissue implant preservation abutment to resurface the outer shell.

Improvements Over Prior Art:

Following are some improvements of the invention over known implant apparatuses and methods:

Preservation of the soft tissue architecture after the immediate removal of a tooth.

Support of the soft tissues to prevent collapse of bone and soft tissue during healing.

Creation a soft tissue "seal" of the replacement temporary to the overlying soft tissues. A soft tissue seal of the residual soft-tissue socket of an extracted tooth in which an immediate implant has been placed.

Produce soft tissue adhesion by providing direct physically contact between the prosthesis and surrounding soft tissue socket.

Placement of a single interface between implant and prosthesis that is below the soft tissue proximal heights at or below the level of supporting bone.

One-piece prosthetic design that is a temporary that is screw retained.

Prosthesis emergence profile is over-contoured to provide an adequate soft-tissue seal and soft-tissue support to the soft tissues to preserve the natural architecture of the gingival tissues.

Prosthesis is under-contoured to provide an adequate soft tissue seal between prosthesis and soft tissue socket to support the soft tissues to preserve the natural architecture of the gingival tissues.

The supra-gingival contour of the tooth prosthesis is identical to the natural tooth while the sub-gingival possesses a emergence profile contour that is either over-contoured or under-contoured to compensate for the lack of ideal position of an implant in the vertical, horizontal, and buccal-lingual, mesial-distal angulations.

Anti-rotational prosthesis screw-retained temporary prosthesis. Anti-rotational features in the implant/abutment connection.

The temporary abutment is constructed directly chair-side utilizing a prefabricated series of anatomic shells who's central access is eccentric to allow either an over-contoured or under-contoured subgingival emergence profile thereby allowing adequate support of the soft tissue and ensuring a seal being formed between the soft tissue socket and the temporary prosthesis.

The temporary abutment is anticipated to prefabricate in a variety of sizes and elliptical shapes of the root surfaces. Different vertical heights will be provided. The shapes will be designed to represent replacement of an extracted tooth.

Antimicrobial Surface and/or material to be used.

Incorporation of a microtexture on the surface of the temporary that has a regular geometric configuration to encourage soft-tissue connection.

Use of a specialized bur that creates a regular pattern on the surface of the temporary.

The following designs are anticipated, but not limited to:

Temporary transmucosal (root form) implant temporary shell root form in the soft-tissue zone from the platform head of the implant to the free-gingival margin.
   a. The superior 1-3 mm may be smooth surfaced to provide a plaque free zone.
   b. Inferior surface (below the 1-3 mm plaque zone) may be textured to encourage soft tissue adhesion.
   c. Surface treatment of the shell by steam cleaning.

The transmucosal temporary component of the invention makes the physical and structural connection between the dental implant and the overlying soft-tissues for the final connection to a tooth replacement prosthesis visible inside the mouth.

The implant 30 and screw 50 are made of surgical steel or other metals such as titanium/titanium alloy. The post is made of steel, ceramic of other durable material such as gold alloy, e.g. AuPdAg (gold-palladium-silver). The shell is zirconium oxide ceramic or other suitable material as listed above. The luting compound is, for example resin or resin-ionomer. The tooth-form temporary 70 is made of material such as polymethyl methacrylate (PMMA), polyetheretherketone (PEEK), lithium disilicate, or zirconium dioxide.

While specific embodiments of the invention have been shown and described in detail to illustrate the application of the principles of the invention, it will be understood that the invention may be embodied otherwise without departing from such principles.

What is claimed is:

1. A soft-tissue preservation, dental implant arrangement, comprising:
   a hollow shell (10) with an interior volume and a shell axis (12), the hollow shell having an outer bio-compatible surface for engaging a soft-tissue socket that is left in gingival tissue after a tooth has been extracted from a bone socket under the gingival tissue, the shell having a first outer perimeter (16) adapted for placement toward the bone socket and a second outer perimeter (18) adapted for placement adjacent an outer surface of the gingival tissue around the soft-tissue socket, the first outer perimeter being smaller than the second outer perimeter so that the shell tapers outwardly from the first outer perimeter to the second outer perimeter, the second perimeter being asymmetrically scalloped with opposite distal and mesial peaks (20, 22) and opposite lingual and facial valleys (24, 26) between the peaks, and the shell being sized engaging against the soft-tissue socket without gaps;
   a dental implant (30) having an implant axis (32) and being adapted for placement in the bone socket;
   a hollow temporary post (40) having an upper end portion and a lower end portion, the temporary post extending through the interior volume of the hollow shell;
   a luting compound filling the interior volume between the shell and the temporary post and setting solid for fixing the shell to the temporary post, wherein the first outer perimeter is situated above the lower end portion such that the lower end portion can be engaged with the implant;
   the hollow temporary post and the hollow shell rigidly connected to the dental implant with no other direct connection between the shell and the implant so that the outer surface of the shell can engage against the soft-tissue socket without gaps and without requiring alignment of the shell axis (12) to the implant axes (32).

2. The arrangement of claim 1, wherein the lingual valley (24) is lower than the facial valley (26).

3. The arrangement of claim 1, wherein the lingual valley (24) is higher than the facial valley (26).

4. The arrangement of claim 1, wherein the lingual valley (24) is generally the same height as the facial valley (26).

5. The arrangement of claim 1, wherein the distal and mesial peaks are not in a common plane with the shell axis.

6. The arrangement of claim 1, wherein the lingual valley (24) is lower than the facial valley (26) and the distal and mesial peaks are not in a common plane with the shell axis.

7. The arrangement of claim 1, wherein the lingual valley (24) is higher than the facial valley (26) and the distal and mesial peaks are not in a common plane with the shell axis.

8. The arrangement of claim 1, wherein the lingual valley (24) is generally the same height as the facial valley (26) and the distal and mesial peaks are not in a common plane with the shell axis.

9. The arrangement of claim 1, including a tooth-form temporary (70) attached at the second perimeter (18) for temporarily replacing an extracted tooth.

10. The arrangement of claim 1, including a screw (50) extending in the post (40) and connecting the post to the implant (30), and a plug (80) in the post (40) above the screw and in the luting compound (60) for providing access to the screw when the plug is removed for disconnecting the post from the implant.

11. A dental implant arrangement, comprising:
- a hollow shell (10) with an interior volume and an outer bio-compatible surface for engaging a soft-tissue socket left immediately after a tooth has been extracted from a bone socket, the shell having an inner perimeter (16) and an outer perimeter (18), the outer perimeter being asymmetrically scalloped with opposite distal and mesial peaks (20, 22) and opposite lingual and facial valleys (24, 26) between the peaks, and the shell being sized for closely engaging against the soft-tissue socket without gaps;
- a dental implant (30) having an implant axis (32) and being adapted for placement in the bone socket;
- a hollow temporary post (40) having an upper end portion and a lower end portion, the lower end portion being rigidly connected to and coaxial with the dental implant, the temporary post extending through the interior volume of the hollow shell; and
- an initially fluid luting compound filling the interior volume between the shell and the temporary post and setting solid for fixing the shell to the dental implant, wherein the outer perimeter is situated above the lower end portion such that the lower end portion can be engaged with the implant;
- the hollow temporary post and the hollow shell rigidly connected to the dental implant with no other direct connection between the shell and the implant so that the outer surface of the shell can engage against the soft-tissue socket without gaps and without requiring any particular alignment between the shell and the implant.

12. The arrangement of claim 11, wherein the lingual valley (24) is lower than the facial valley (26).

13. The arrangement of claim 11, wherein the lingual valley (24) is higher than the facial valley (26).

14. The arrangement of claim 11, wherein the lingual valley (24) is generally the same height as the facial valley (26).

15. The arrangement of claim 11, wherein the distal and mesial peaks are not in a common plane with the shell axis.

* * * * *